US008923773B1

(12) United States Patent
Gitlin et al.

(10) Patent No.: US 8,923,773 B1
(45) Date of Patent: *Dec. 30, 2014

(54) MINIMALLY INVASIVE NETWORKED SURGICAL SYSTEM AND METHOD

(71) Applicants: Richard D. Gitlin, Tampa, FL (US); Gabriel E. Arrobo, Tampa, FL (US); Thomas P. Ketterl, Tampa, FL (US)

(72) Inventors: Richard D. Gitlin, Tampa, FL (US); Gabriel E. Arrobo, Tampa, FL (US); Thomas P. Ketterl, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/099,428

(22) Filed: Dec. 6, 2013

Related U.S. Application Data

(63) Continuation-in-part of application No. 13/716,905, filed on Dec. 17, 2012, now abandoned, which is a continuation of application No. 12/608,580, filed on Oct. 29, 2009, now Pat. No. 8,358,981.

(60) Provisional application No. 61/109,368, filed on Oct. 29, 2008.

(51) Int. Cl.
*H04B 7/00* (2006.01)
*A61B 1/00* (2006.01)
*A61B 5/00* (2006.01)
*H04W 40/00* (2009.01)
*H04M 1/00* (2006.01)

(52) U.S. Cl.
CPC ........... *A61B 1/00006* (2013.01); *A61B 5/0024* (2013.01); *H04W 40/00* (2013.01)
USPC ..................................... 455/66.1; 455/575.6

(58) Field of Classification Search
CPC ... A61B 1/00016; A61B 1/041; A61B 5/0024
USPC ........ 455/66.1, 575.6, 569.1, 100, 41.1, 41.2, 455/41.3; 607/60, 3
See application file for complete search history.

(56) References Cited

U.S. PATENT DOCUMENTS

| | | |
|---|---|---|
| 5,604,531 A | 2/1997 | Iddan et al. |
| 6,402,689 B1 | 6/2002 | Scarantino et al. |
| 6,546,272 B1 | 4/2003 | MacKinnon et al. |
| 7,009,634 B2 | 3/2006 | Iddan et al. |
| 7,214,182 B2 | 5/2007 | Shimizu et al. |
| 8,358,981 B1 * | 1/2013 | Gitlin et al. .................. 455/66.1 |
| 8,416,342 B1 | 4/2013 | Gitlin et al. |
| 2006/0009818 A1 * | 1/2006 | Von Arx et al. ................. 607/60 |
| 2007/0255098 A1 | 11/2007 | Wang et al. |
| 2007/0270651 A1 | 11/2007 | Gilad et al. |

* cited by examiner

*Primary Examiner* — Eugene Yun
(74) *Attorney, Agent, or Firm* — Nilay J. Choksi; Smith & Hopen, P.A.

(57) ABSTRACT

A system for performing non-invasive networked medical procedures including a number of in vivo medical devices, a communication path between at least two of the devices, an ex vivo control unit to control the behavior of the devices, and a wireless communication path between the control unit and at least one of the devices. An associated method for performing non-invasive networked medical procedures is also provided. Further included is a simulation method that utilizes accurate electromagnetic field simulations, using a software based test bench, to determine the maximum allowable transmitted power levels from in vivo devices to achieve a required bit error rates (BER) at an in vivo or ex vivo node (receiver) while maintaining the specific absorption rate (SAR) under a required threshold.

20 Claims, 16 Drawing Sheets

MINIMALLY INVASIVE NETWORKED SURGICAL SYSTEM AND METHOD

CROSS REFERENCE TO RELATED APPLICATIONS

This application is a continuation-in-part of and claims priority to U.S. Non-provisional application Ser. No. 13/716,905, entitled "Minimally Invasive Networked Surgical System and Method", filed Dec. 17, 2012, which is a continuation of and claims priority to U.S. Non-provisional application Ser. No. 12/608,580, entitled "Minimally Invasive Networked Surgical System and Method", filed Oct. 29, 2009, which claims priority to U.S. Provisional Application No. 61/109,368, entitled, "Non-Invasive Networked Surgery", filed Oct. 29, 2008, all of which are incorporated herein by reference.

FEDERALLY SPONSORED RESEARCH OR DEVELOPMENT

This invention was made with Government support under Grant No. IIP-1217306 awarded by the National Science Foundation. The government has certain rights in the invention.

BACKGROUND OF THE INVENTION

1. Field of the Invention

This invention relates, generally, to a system and method device for minimally invasive surgical procedures. More specifically, it relates to a network of various in vivo medical devices.

2. Brief Description of the Prior Art

As minimally invasive surgical (MIS) procedures become increasing sophisticated, new functions will be needed to realize successful surgical outcomes. For example, conventional laparoscopy places a limit on the number of devices that can be inserted in the body. In addition, these devices have limited positioning capabilities and may compete or interfere with the preferred motion or position of another instrument.

Devices and methods for performing in vivo imaging of passages or cavities within a body are known in the art, and there are self-propelled devices known in the art. However, these conventional technologies use a single device (e.g. a camera pill), which are difficult to inject into the body and properly position and navigate due to their size. Having a single device also limits the ability of the surgeon to perform multiple tasks in a single session, or view the progress of the surgical procedure from the most advantageous angle.

Generally, wireless communication for biomedical applications is a research topic that has seen a tremendous increase in attention in recent years (C. Castro, A, Alqassis, S. Smith, T. Ketterl, Y. Sun, S. Ross, A. Rosemurgy, P. Savage, and R. Gitlin, "A Wireless Robot for Networked Laparoscopy," IEEE. Transactions on Biomedical Engineering, pp. 930-936, April 2013; A. Alqassis, T. Ketterl, C. Castro, R. Gitlin, S. Ross, Y. Sun, and A. Rosemurgy, "MARVEL IN VIVO WIRELESS VIDEO SYSTEM," Technology & innovation, vol. 14, no. 3, pp. 329-340, March 2012; G. E. Arrobo and R., D. Gitlin, "New approaches to reliable wireless body area networks," in IEEE International Conference on Microwaves, Communications, Antennas and Electronics Systems (COMCAS 2011), Tel Aviv, Israel, 2011, pp. 2-6; M. Chen, S. Gonzalez, A. Vasilakos, II Cao, and V. C. M. Leung, "Body Area Networks: A Survey," Mobile Networks and Applications, vol. 16, pp. 171-193, August 2010; M. A. Hanson, H, C, Powell, A. T. Barth, K, Ringgenberg, B. H, Calhoun, J. H Aylor, and J. Each, "Body Area Sensor Networks: Challenges and Opportunities," Computer DOI—10.1109/MC.2009.5, vol. 42, no. 1, pp. 58-65, 2009; Huasong Cao, V. Leung, C. Chow, and H Chan, "Enabling technologies for wireless body area networks: A survey and outlook." Communications Magazine, IEEE, vol. 47, no. 12, pp. 84-93, 2009).

Implanted sensors and actuators for medical applications have the potential of being critical components in advanced health care delivery by reducing the invasiveness of a number of medical procedures. Such applications include, but are not limited to, internal health monitoring and drug administration (E. Piel, A. Gonzalez-Sanchez, H. Gross, and A. J. C. van Gemund, "Spectrum-Based Health Monitoring for Self-Adaptive Systems," in Self Adaptive and Self-Organizing Systems (SASO), 2011 Fifth IEEE International Conference on, 2011, pp. 99-108; E. Y. Chow, B. Beier, Y. Ouyang, W. J. Chappell, and P. P. Irazoqui, "High frequency transcutaneous transmission using stents configured as a dipole radiator for cardiovascular implantable devices," in IEEE MTT-S International Microwave Symposium Digest, 2009, pp. 1317-1320).

Current medical sensors use dedicated systems (dedicated system for each device) for wireless communications, data processing, and backend databases. These systems rely on low data rate communications and best-effort processing of aggregate data. However, one must consider specific absorption rate (SAR) levels and bit-error-rate (BER) when utilizing this technique.

SAR levels of radio frequency (RF) radiation produced by cellular phone activity near the human head have already been extensively investigated (M. H. Mat, M. F. B. A. Malek, A. Omar, M. S. Zulkefli, and S. H. Ronald, "Analysis of the correlation between antenna gain and SAR Levels inside the human head model at 900 MHz," in Asia-Pacific Symposium on Electromagnetic Compatibility (APEMC), 2012, pp. 513-516; M. Ahmed, "Investigating Radiation Hazard and Safety Aspects of Handheld Mobile," in Third international Conference on Mobile Ubiquitous Computing, Systems, Services and Technologies, 2009, pp. 1-9; C. Lazarescu, I. Nica, and V. David, "SAR in human head due to mobile phone exposure," in E-Health and Bioengineering Conference (EHB), 2011, 2011, pp. 1-4). SAR effects near other parts of the human body, such as in body area networks (BAN) applications (IEEE P802.15 Working Group for Wireless Personal Area Networks (WPANs), "Channel Model for Body Area Network (BAN).") have also seen increased attention (T. Koike-Akino, "SAR Analysis in Dispersive Tissues for In vivo UWB Body Area. Networks," in Global Telecommunications Conference, 2009. GLOBECOM 2009. IEEE, 2009, pp. 1-6).

However, research in SAR levels produced by in vivo devices has so far been very limited (S. Aoyama, D. Anzai, and J. Wang, "SAR evaluation based on required BER performance for 400 MHz implant BANs," in Asia-Pacific Symposium on Electromagnetic Compatibility, 2012, pp. 365-368). Although, in Aoyama et al., the authors provided results for specific absorption rate SAR and BER evaluation for implant BAN's operating at the 400 MHz ISM band. Due to an increasing need to provide high data rate in in vivo communications, however, it is essential to evaluate the SAR under BER requirements at higher frequencies. Such results will give the system designer guidance about whether a relay network will be needed to attain reliable communications through the extremely lossy and dispersive in vivo channel (T. P. Ketterl, G. E. Arrobo, A Sahin, T. J. Tillman, H Arslan, and R. D. Gitlin, "In vivo wireless communication channels," in IEEE 13th Annual Wireless and Microwave Technology Conference, 2012, pp. 1-3).

Accordingly, what is needed is unified system or method for controlling a networked plurality of in vivo medical devices in the body of a subject, while reducing clutter and improving the quality and reliability of communications. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved wireless communication between in vivo sensors/actuators and ex vivo transceivers for performing minimally invasive networked surgical procedures is now met by a new, useful, and nonobvious invention.

The present invention includes a system and associated method for performing minimally invasive, networked medical procedures. The system includes a number of in vivo medical devices, such as imaging devices, sensors and actuators, power sources, cutting tools (physical, optical, ultrasound, etc.), and other ancillary devices, and a communication path between at least two of the in vivo medical devices. The system further includes an ex vivo control unit to control the behavior of the in vivo medical devices and a wireless communication path between the control unit and at least one of the in vivo medical devices. The system may further include a second wireless communication path between at least one of the in vivo medical devices and an ex vivo system.

The communications and control units may be combined into a single unit and their communications paths may be shared. The in vivo medical devices may be electronically addressable and electronically controllable and form a distributed wireless network whose capabilities exceed that of individual devices. The in vivo medical devices may also be magnetically controllable. There also may be a number of wireless communication paths between the control unit and each of the in vivo medical devices. These wireless communications links, or additional wireless links, also provide a two-way communication path for the in-vivo devices to communicate a variety of information with external systems.

The method of performing networked medical procedures includes providing a number of in vivo medical devices and a communication between at least two of the in vivo medical devices. The method further includes providing an ex vivo control unit to control the behavior of the in vivo medical devices and providing a wireless communication path between the control unit and at least one of the in vivo medical devices. The method also includes controlling the behavior of the in vivo medical devices from outside the body using the wireless communication path between the control unit and the at least one of the in vivo medical devices. The method may further include providing a second wireless communication path between at least one of the in vivo medical devices and an ex vivo system. The second wireless communication path may be a duplex wireless communication path.

Controlling the behavior of the in vivo medical devices from outside the body using the wireless communication path between the control unit and at least one of the in vivo medical devices may include generating a control signal at the control unit and transmitting the control signal over the wireless communication path to a first in vivo medical device. Controlling the behavior of the in vivo medical devices from outside the body may also include receiving the control signal at the first in vivo medical device, generating a second control signal at the first in vivo medical device, and transmitting the second control signal over the communication path between the first in vivo medical device and a second in vivo medical device to the second in vivo medical device.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description taken in connection with the accompanying drawings, in which.

DETAILED DESCRIPTION OF THE PREFERRED EMBODIMENT

Figure 1:
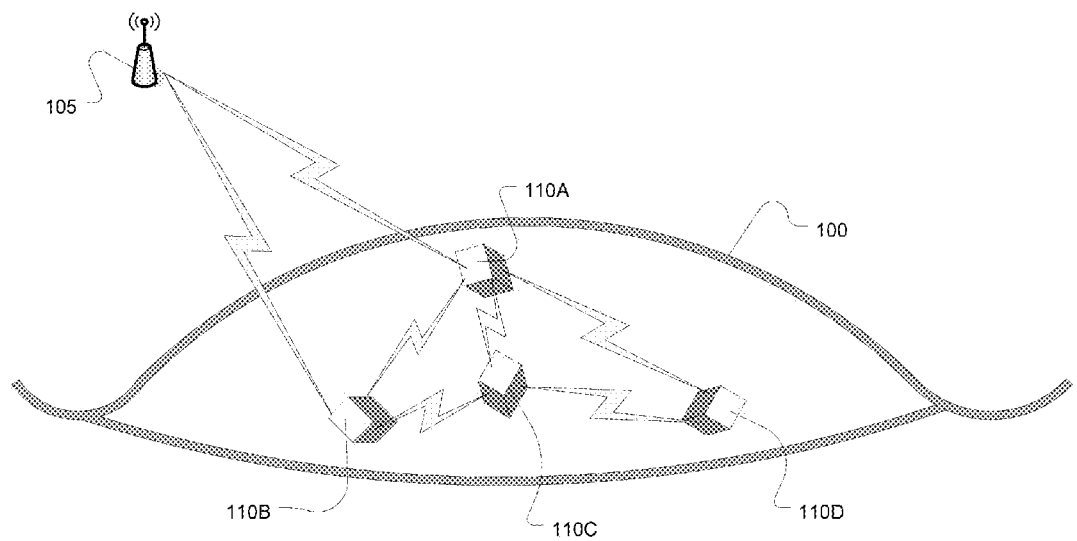
FIG. 1 is a general diagram of a plurality of in vivo medical devices, which are networked together and controlled wirelessly via a wireless access point located outside the body, in accordance with an embodiment of the present invention.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention includes a system and associated method for performing non-invasive medical procedures. The system includes a number of networked devices for in vivo medical applications, whereby the system creates a wireless network of cyber-physical in vivo devices that enhances and enables innovative non-invasive and MIS surgical and other procedures. Typical applications include, but are not limited to, procedures in the gastrointestinal tract of a human being. The system and method allow for the performance of complex and time-consuming surgeries to be minimally invasive and in some cases with only local or no anesthesia. This increases the safety of the surgery and minimizes patient anxiety. The current invention can further provide new (asymmetric) communications and multihop networking paradigms for devices to achieve reliable, high-throughput and near zero latency intra-body wireless communications and networking. This system is capable of coping with the complexity of an in vivo multipath RF channel.

The invention includes a plurality of in vivo medical devices of the same or different types, such as imaging devices, sensors, power sources, collectors, and "cutting" tools (physical, optical, ultrasound, lasers, etc.). There also may be multiples of the same type of device. For example, multiple batteries may be used so that the devices do not prematurely run out of power.

The devices are controlled by one or more external (ex vivo) control units, such as an expert system. The invention may include other external (ex vivo) systems in addition to the control unit. Examples of such an external system include a server and an external display system for displaying images from an in vivo video camera. The invention may further include one or more external (ex vivo) communication units, such as an external wireless access point, which transmit data between the in vivo medical devices and the one or more external control units or other external systems.

Such ex vivo control units may be implemented on smartphones or other devices, such has those capable of implementing a 32-bit processor architecture and having low power consumption with high energy density battery. However, any device is contemplated for the purpose of these communications.

The invention may also include one or more communication paths between one or more of the in vivo medical devices and the external system(s). These communication paths may carry control signals or any other type of communication required by the system. The communication path may either be a separate communications link with dedicated resources (e.g. separate frequency, time slot, or code, for each "path") or an addressable logical link in a shared medium (such as a packet network). Each communication path may be uni- or bi-directional depending on the needs of the system. For example, an in vivo video camera may have a dedicated communication path between it and an external control and display system. The control signal would be sent from the external system to the video camera via the communication path and the camera would send images to the external system via the same communication path. Alternatively, there may be more than one communication path between two devices—one carrying control signals and another for communication.

The invention may also include one or more communication paths between the in vivo medical devices. These communication paths may carry control signals or any other type of communication required by the system. The communication paths may also relay information received by one in vivo medical device from an external system to another in vivo medical device. Each communication path may be uni- or bi-directional depending on the needs of the system.

Each of the devices may be externally electronically addressable. Each device may be externally controllable (e.g., via wireless, magnetic, or other means). Each device may perform a required task in response to externally generated control signals. The device may be positioned in response to the control commands. Movement of the devices may be accomplished in a variety of ways including mini motors and thrusters, as well as the use of magnets. The devices may have means of acquiring position or other information (e.g., a GPS). The devices may be capable of originating communications with the external systems or with other in vivo devices. These communications may for example, communicate the information acquired by the device and/or the status or condition of the device.

The devices may assume a hierarchical, mesh, tree, ad-hoc, or other architecture that is appropriate for the application.

Exemplary implantable device applications may include, without limitation, imaging applications (implanted devices with camera and light source for transmission of image data; e.g., camera pill, laparoscopic cameras, etc.), sensors (implanted devices that can test for biological conditions or symptoms and transmit data to external receivers or regulate other medical devices or actuators; e.g., implanted RFID sensors, glucose monitor, EKG sensors, etc.), and actuators (implanted devices that perform specific actions in response to internal programming or an external stimulus; e.g., neuro-stimulator, drug delivery, insulin pumps, etc.).

Figure 9:
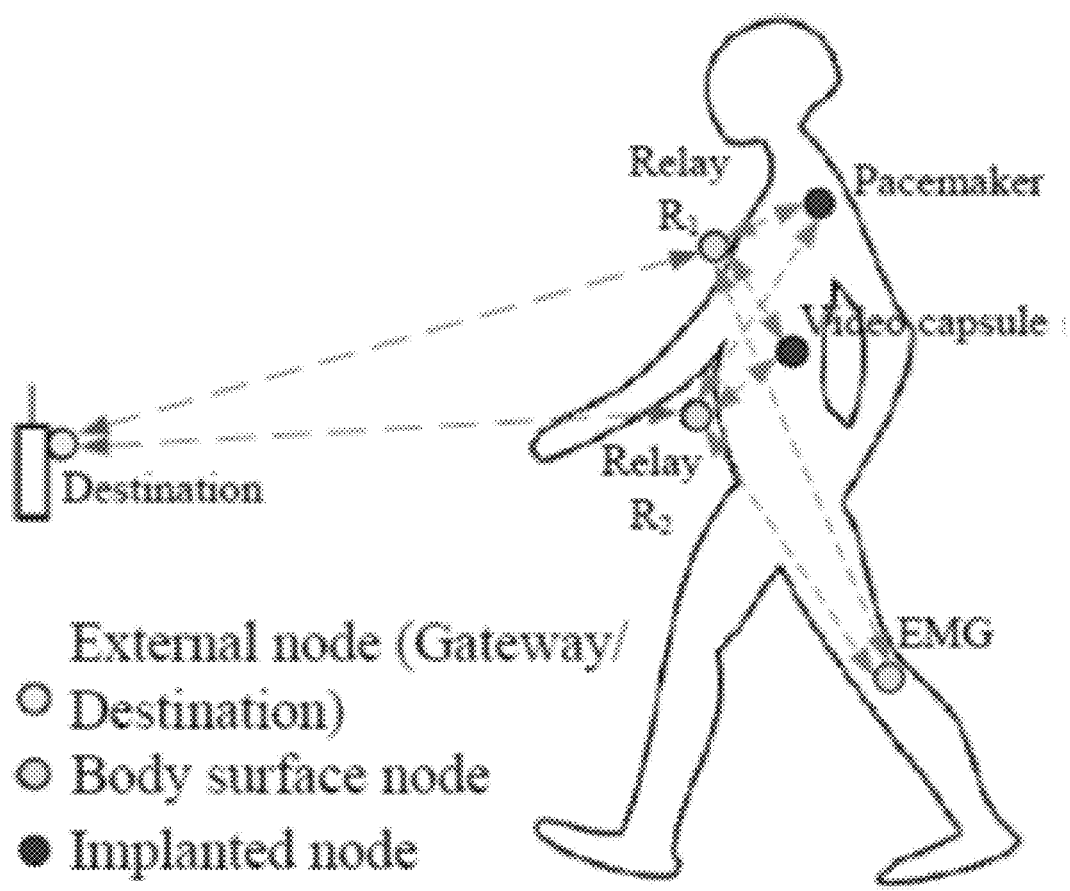
FIG. 9 is a human body schematic showing the destination/hub/gateway (external node), body surface nodes, and implanted nodes, and the relationships therebetween.

A generalized example of the present invention is shown in FIG. 1. In this example, plurality of in vivo medical devices 110A-110D are networked together and controlled wirelessly via wireless access point 105 located outside body cavity 100 and gateway on the body (not shown in this figure, but seen in FIG. 9, where the wireless access point is communicatively coupled with the gateway, and the gateway is communicatively coupled to in vivo medical devices 110A-110D).

Figure 2:
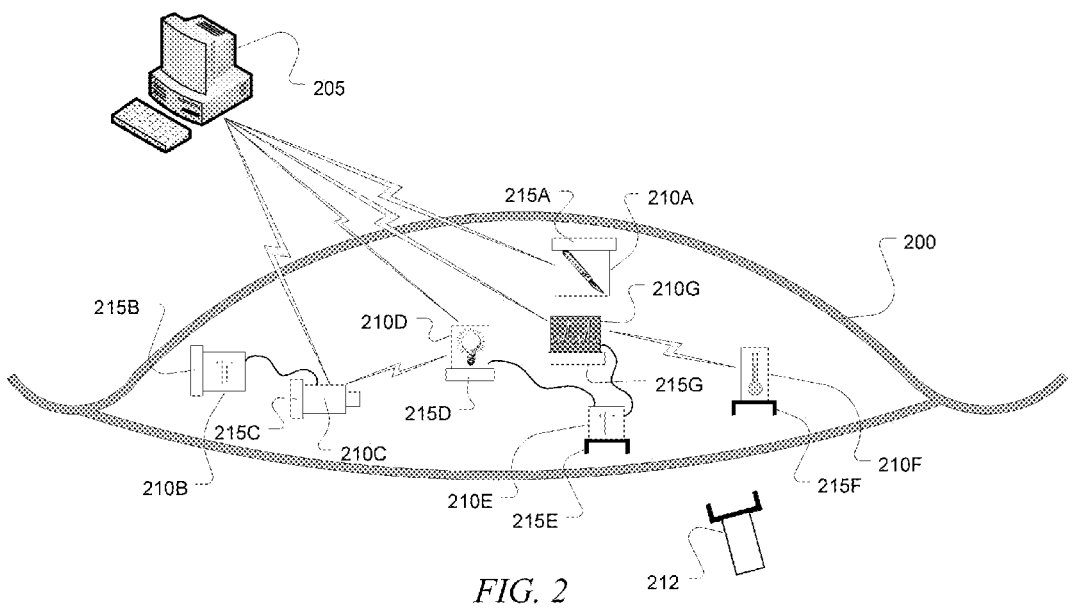
FIG. 2 is a diagram of a plurality of exemplary in vivo medical devices, which are networked together and controlled wirelessly by a control unit located outside the body, in accordance with an embodiment of the present invention.

Another example is shown in FIG. 2. Here, the in vivo medical devices include cutting tool 210A with positioning device 215A, battery 210B with positioning device 215B, camera 2100 with positioning device 2150, light 210D with positioning device 215D, battery 210E with magnet 215E, sensor 210F with magnet 215F, and monitor 210G with positioning device 215G. Positioning devices include any device that provides movement to the respective in vivo medical device, such as mini-motors or thrusters. In addition, external magnet 212 may be used in conjunction with magnet 215E or 215E to move battery 210E or sensor 210F, respectively.

In vivo medical devices 210A-210G may be connected to one or more of each other via a wired or wireless connection. For example, in FIG. 2, camera 210C has a wired connection with battery 215B and a wireless connection with light 210D. Further, any number of in vivo medical devices 210A-210G may be wirelessly connected to an external control unit, here computer 205. In this example, four in vivo medical devices are wirelessly connected to computer 205—cutting tool 210A, camera 210C, light 210D, and monitor 210G.

High Data Rate Communication in carrying out certain embodiments of the current invention, high data rate communication systems (e.g., in point-to-point systems, networks, etc.) can be developed between implanted and external receivers for use during minimally invasive surgical procedures. For example, one application that may require high data transmission capabilities is high definition (HD) video from the in vivo camera modules.

To reliably transmit a high data rate signal through the in vivo channel requires a given signal-to-noise ratio (SNR) and appropriate forward error control. One method to monitor the performance of a digital communication system is to measure the BER of the communication. A low BER is needed for high communication performance which depends on the transmission power to obtain the required SNR. However, since data is being transmitted through or near the human body, the signal levels are limited to the safety guidelines set by the Federal Communications Commission (FCC). The method described herein allows the communication system designer to simultaneously monitor the BER of the system and the resulting SAR levels of the in vivo transmitter.

An example of a type of network that can be used is a wide body area network, which can transmit at low power to protect patients against harmful health effects associated with the RF emissions as well as to extend the battery lifetime of the node (device). SAR is the rate at which the RF energy is absorbed by a body volume or mass and has units of watts per kilogram (W/Kg). This sets a limit on the transmitted power. The SAR limit is frequency dependent, since it depends on the conductivity of the material, which changes with frequency in human organs/tissues. Due to this limitation on the specific absorption rate, it is not possible to increase the transmission power beyond a certain level to overcome transmission errors. By networking the in vivo nodes via relay nodes, it is possible to transmit the in vivo sensors' information to external nodes while keeping the SAR within allowed limits.

The methodology described herein that utilizes accurate electromagnetic field simulations to study the maximum allowable transmitted power levels from a network of in vivo devices to achieve a required BER at the external or in vivo node (receiver) while maintaining the SAR under a required threshold. The BER of the communication can be calculated using the derived power threshold for a given modulation scheme. These results can be used to optimize the transmitted power levels while assuring that the safety guidelines, given by the FCC, in terms of the resulting SAR of transmitters placed in any location inside the human body are met. A software-based test bench is utilized to facilitate the implementation of field solver solutions directly into system simulations. This test bench allows the system designer to easily monitor the performance of the communication while, at the same time, observe the SAR levels using highly accurate in vivo models.

In the following experimentation, SAR levels and communication BER were calculated using the software-based test bench, where the system designer can monitor the performance of the communication, while simultaneously observing the SAR levels in highly accurate in vivo environments. The goal of the experimentation is to study the maximum allowable transmitted power levels from in vivo devices to achieve a required BER at the ex vivo node (receiver) while maintaining the SAR under a required threshold The dynamic link capabilities between the ANSYS Designer, which is a complete RF circuit and systems simulation tool, and ANSYS HFSS, a high frequency numerical electromagnetic field simulator, were utilized, along with a highly accurate human body model in HFSS, to create the test bench.

Simulation tests were run to determine any limitations that might be experienced by the networked in vivo medical devices in a human body. The tests utilized accurate electromagnetic field simulations to study the maximum allowable transmitted power levels from in vivo devices to achieve a required BER at the external node (receiver), while maintaining the SAR under a required threshold. The BER of the communication can be calculated using the derived power threshold for a given modulation scheme. These results can be used to optimize the transmitted power levels while assuring that the safety guidelines—in terms of the resulting SAR of transmitters placed in any location inside the human body— are met. To evaluate SAR and BER, a software-based test bench that allows an easy way to implement field solver solutions directly into system simulations was developed. To demonstrate the software-based test bench design, a complete OFDM-based communication (IEEE 802.11g) for the in vivo environment was simulated. Results showed that for cases when noise levels increased or the BER became more stringent, a relay network or the use of multiple receiver antennas, such as in a MIMO system, would be desired to achieve high data rate communication.

SAR and BER

The interaction of electromagnetic fields with human body tissues cause localized tissue heating and damage in the vicinity of radiating sources at unsafe power levels. To restrict the amount of radiation that the living tissue can be subjected to, strict guidelines were set by the FCC. The SAR, a measurement of how much power is absorbed per unit mass of a conductive material, is defined as follows ("C95.1-200S:

IEEE Standard for Safety Levels With Respect to Human Exposure to Radio Frequency Electromagnetic Fields, 3 kHz to 300 GHz." 2006):

$$SAR = \frac{\sigma |E|^2}{\rho}$$

where $\sigma$ is the electrical conductivity of the material, E is the RMS magnitude of the electric field at a given point, and $\rho$ is the mass density of the material.

The FCC recommended that the SAR level is given for localized areas over any one (1) gram of tissue and for values averaged over the whole human body, also known as local SAR and average SAR, respectively. The limit for the local SAR and average SAR are 1.6 W/kg and 0.08 W/kg, respectively. Since the communication system is limited by how much wireless power can be transmitted near and through the human body, emphasis is placed on optimizing the system performance to ensure that the required BER for reliable wireless in vivo communication is met.

The test bench uses a propagation channel model derived directly in HFSS, meaning that the BER values in each simulation are dependent on the specific antenna performance and placement. Therefore, this test bench allows the system designer not only to decide on optimum system architecture and data rates for reliable communication, but also the flexibility of using different antenna architectures, while also optimizing the antenna designs and placement. With this test bench, in vivo devices can be arbitrarily placed in any part of the human body and easily characterized for SAR levels and BER.

Test Bench

The test bench presented was implemented on ANSYS Designer 8.0 and ANSYS HFSS 15.0. ANSYS Designer allows for design of complete communication systems, both at the system and circuit levels. For digital systems, link quality measurements, such as BER constellation diagrams and eye diagrams, among others, are easily simulated in ANSYS Designer. ANSYS also provides a complete human body model of a detailed adult male with over 300 muscles, organs, and bones with a geometrical accuracy of one (1) mm with realistic frequency-dependent material parameters (conductivity and permittivity) from 20 Hz to 20 GHz. This model is used in HFSS to derive the complete electromagnetic fields produced by an arbitrary radiation source, from which other characteristics, such as scattering parameters and SAR levels, can be directly obtained.

The simulation was performed as follows:
1. The transmit and receive antennas are placed into the HFSS design with the human body model.
2. Field solutions and S-parameter calculations are derived in HFSS over the desired frequency band (and bandwidth).
3. The maximum local SAR levels from the transmit antenna are evaluated in HFSS as a function of frequency. From these data, the maximum allowable power levels can be derived and used in the Designer system simulations.
4. The communication system is set up in Designer.
5. The wireless channel model, derived in the previous HFSS simulation, is used in the Designer system simulations through the direct link between HFSS and Designer.
6. A BER calculation is performed in Designer at various noise levels, using the required power levels (derived in step 3).

Simulation Example

Figure 3:
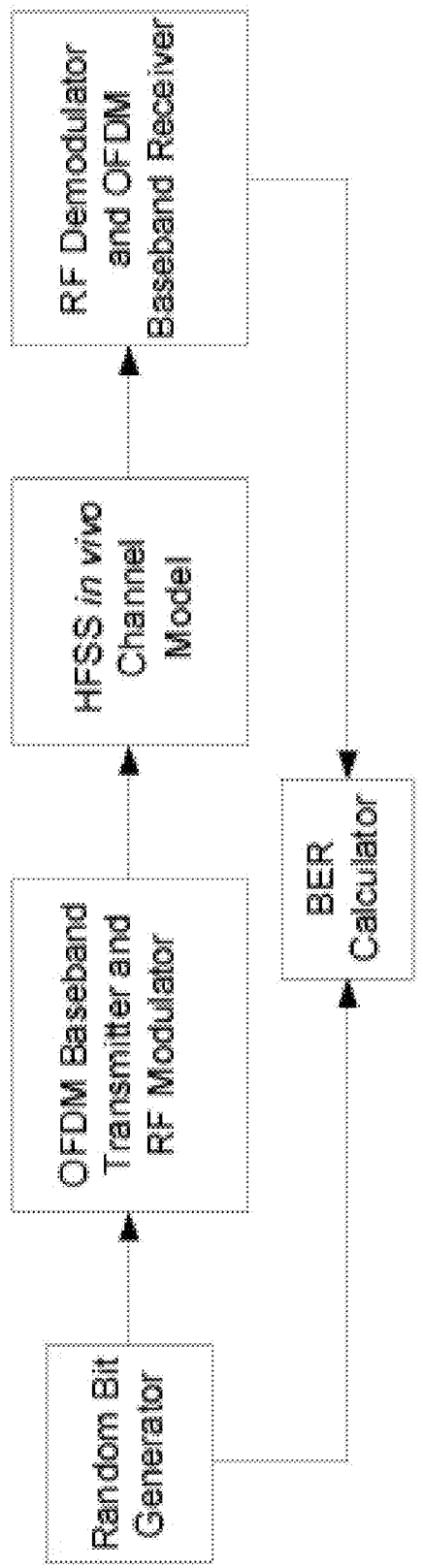
FIG. 3 is a block diagram of a system level simulation showing direct links to the HESS in vivo channel model.

To evaluate the BER performance of in vivo systems, an OFDM-based (802.11g) wireless transceiver model operating at 2.4 GHz was set up with varying transmission and noise power levels, and bit rates in Designer. The OFDM transceiver was simulated using the field simulations obtained from HFSS simulation with the ANSYS human body model from which the maximum allowable local SAR was found, along with the path loss as a function external receiver antenna location. The threshold power derived from these SAR levels was then used in the system simulation to calculate the corresponding BER as a function of external antenna location for data rates of 9, 18, and 36 Mbps. The system block diagram is shown in FIG. 3.

Figures 4A, 4B:
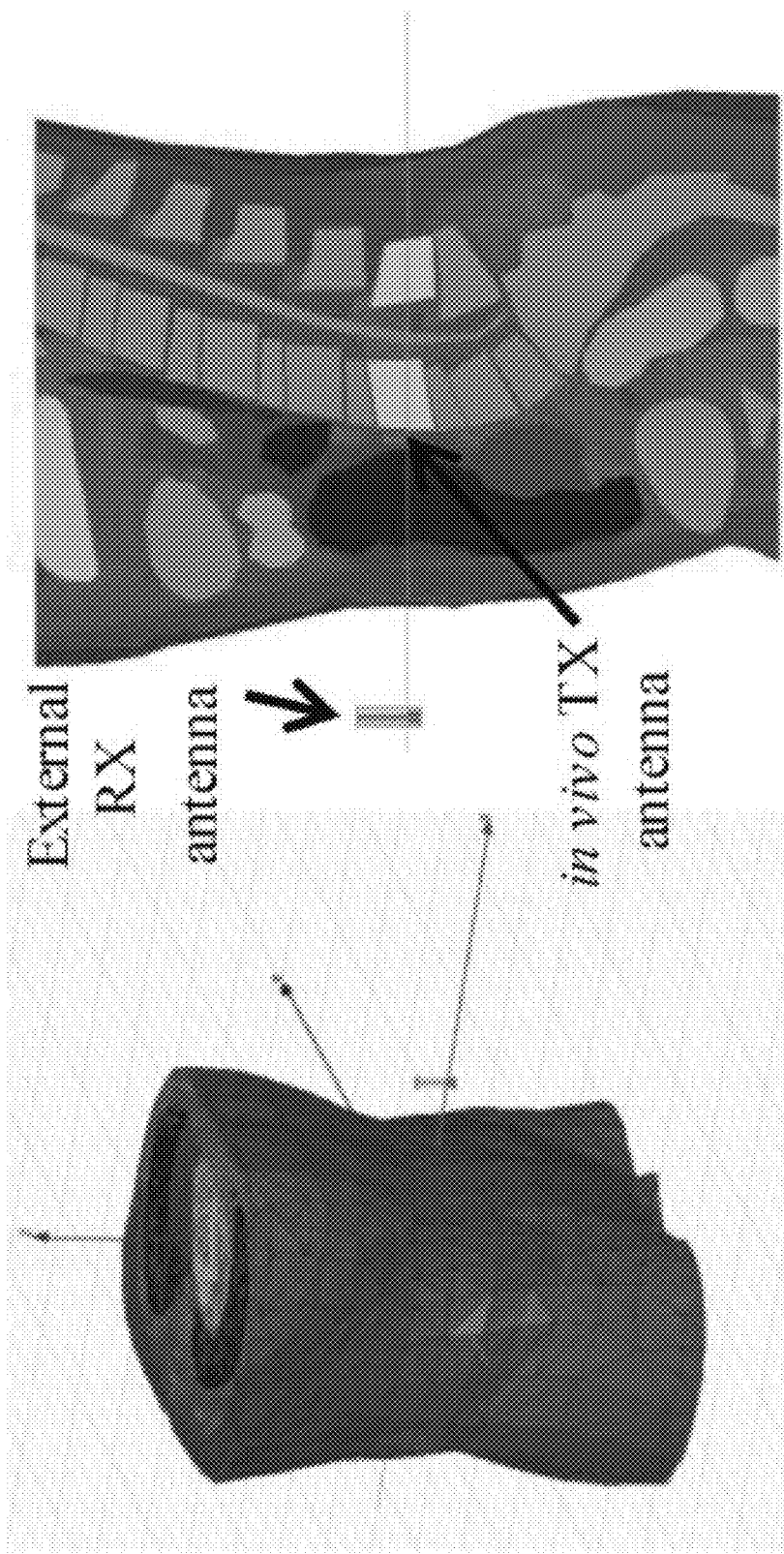
FIG. 4A is truncated HESS human body model used to derive SAR levels on the channel model.
FIG. 4B is a cross section of the model of FIG. 4A showing receive and transmit antenna locations.

For simplicity in this proof-of-concept demonstration, monopole antennas were used in the HFSS simulation, which have been optimized to operate at the design frequency. The in vivo antenna is placed inside the abdomen to simulate placement of transceivers in laparoscopic and intestinal medical applications, and the ex vivo antenna is placed at a distance between one (1) and ten (10) cm in front of the abdomen at the same planar height as the in vivo antenna to obtain the path loss as a function of distance (the in vivo antenna is located 7.8 cm from the abdominal wall). The 3-D model used in HFSS showing the antenna locations can be seen in FIGS. 4A-4B.

For this example, only the local SAR values were calculated since the induced SAR levels are mainly localized near the transmitting antenna (M. H. Mat, M. F. B. A. Malek, A. Omar, M. S. Zulkefli, and S. H. Ronald, "Analysis of the correlation between antenna gain and SAR Levels inside the human head model at 900 MHz," in Asia-Pacific Symposium on Electromagnetic Compatibility (APEMC), 2012, pp. 513-516). HFSS calculates the local SAR levels through the whole body and the test bench provides the maximum value with respect to the input power specified in the system simulation.

Table 1 shows the calculated SAR levels over the required bandwidth for the 2.4125 GHz 802.11g carrier frequency band with one (1) mW of transmit power. Since the SAR scales linearly with power, the maximum allowable transmit power can be calculated, such as 0.412 mW of peak power in this example. The new SAR levels due to the calculated threshold power are also shown in Table 1.

TABLE 1

Calculated SAR levels for different frequencies in the 2.4 GHz band at 1 mW and at the threshold power.

| Frequency GHz | SAR @ 1.0 mW W/kg | SAR @ Threshold Power (0.412 mW) W/kg |
| --- | --- | --- |
| 2.402 | 4.34 | 1.585 |
| 2.412 | 3.25 | 1.562 |
| 2.422 | 3.29 | 1.539 |

Figure 5A:
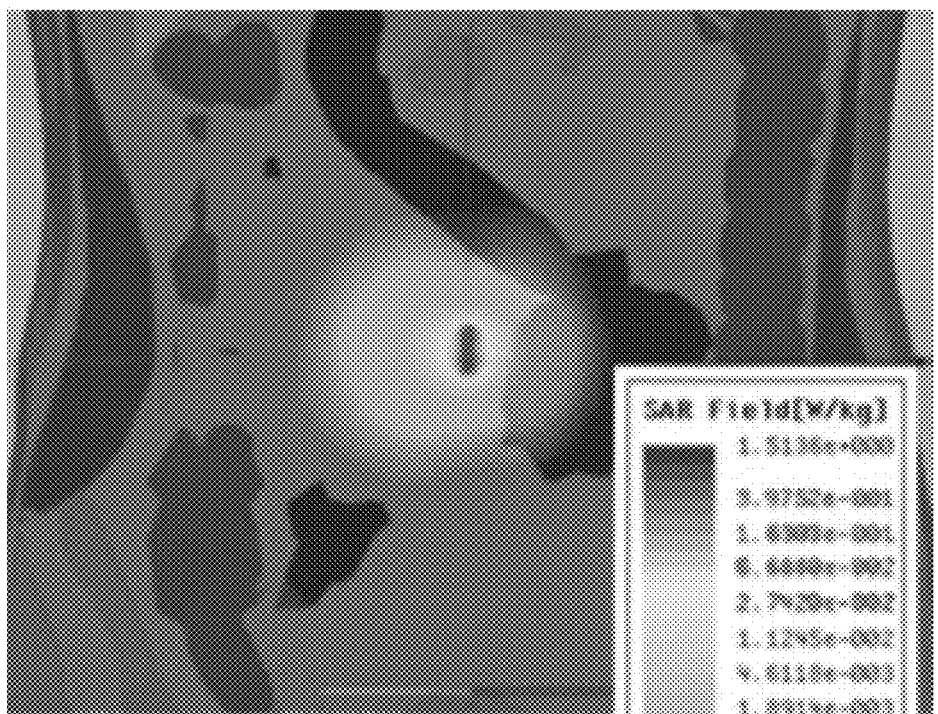
FIG. 5A is a front cross-sectional view of the total SAR generated at 2.412 GHz inside the abdomen at a transmit power of 0.412 mW.
Figure 5B:
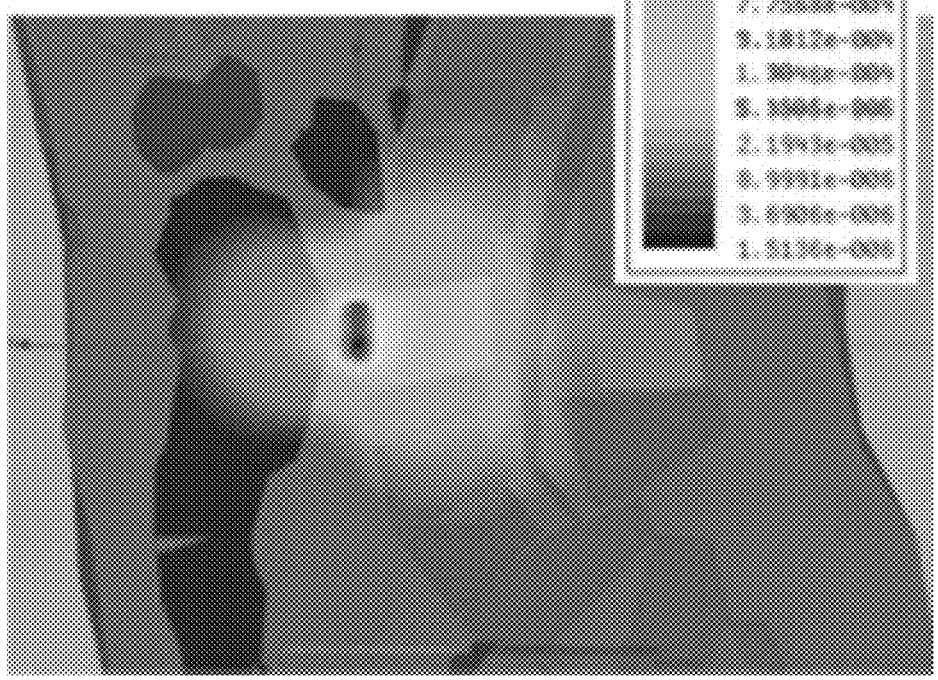
FIG. 5B is a side cross-sectional view of the total SAR generated at 2,412 GHz inside the abdomen at a transmit power of 0.412 mW.

A visual plot of the total SAR levels is shown in FIGS. 5A-5B. FIGS. 5A-5B show the total SAR over a cross-sectional cut when viewed from the front and side, respectively. From these SAR plots, the location of the maximum total SAR generated at 2.412 GHz inside the abdomen at a transmit power of 0.412 mW occurs at points closest to the in vivo monopole antenna. It can also be observed that the SAR reduces very rapidly away from the antenna, which is to be expected since the electric field attenuates with distance in a conductive medium. Achievable distance, as a function of bit rate, between in vim) and external antennas for a BER of $10^{-6}$ can be seen.

The average SAR was also calculated using the threshold power levels calculated from the maximum local SAR. To calculate the average SAR, a one (1) $cm^2$ averaging box was positioned at the location of the maximum SAR. The maximum average SAR was determined in this averaging box and found to be 0.0133 W/kg. This value is within the guideline level of 0.08 W/kg set for the average SAR in the human body.

Figure 6:
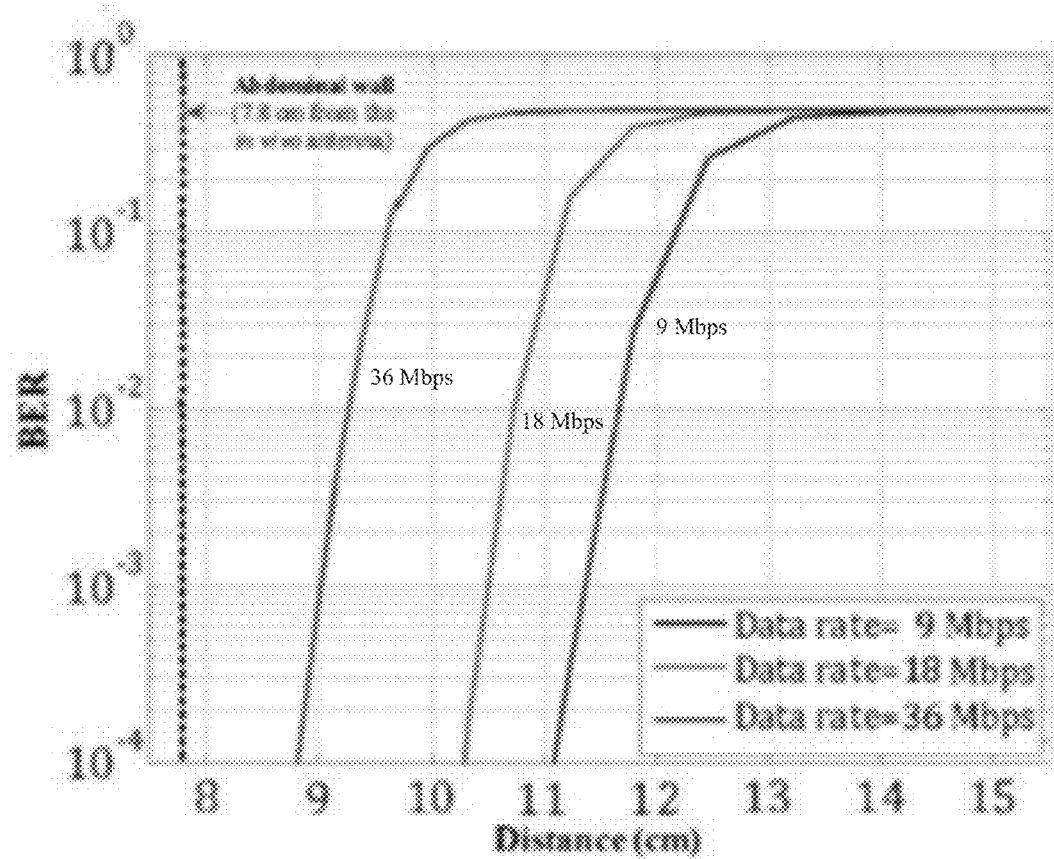
FIG. 6 is a graphical illustration showing BER performance as a function of distance for different data rates at the threshold power (0.412 mW).

The maximum allowable power derived in the HFSS simulation was then used in the OFDM system simulation in Designer. Using a noise level of −101 dBm, the thermal noise with 20 MHz BW, FIG. 6 shows the BER as a function of distance between the external and in vivo antenna with added Gaussian noise for three data rates that follow the 802.11g standard for coding rates and modulation types: 9, 18, and 36 Mbps. In the case when transmitting data at 36 Mbps, the external antenna should be placed within 1.4 cm from the body to achieve a minimum BER of $10^{-3}$.

Figure 7:
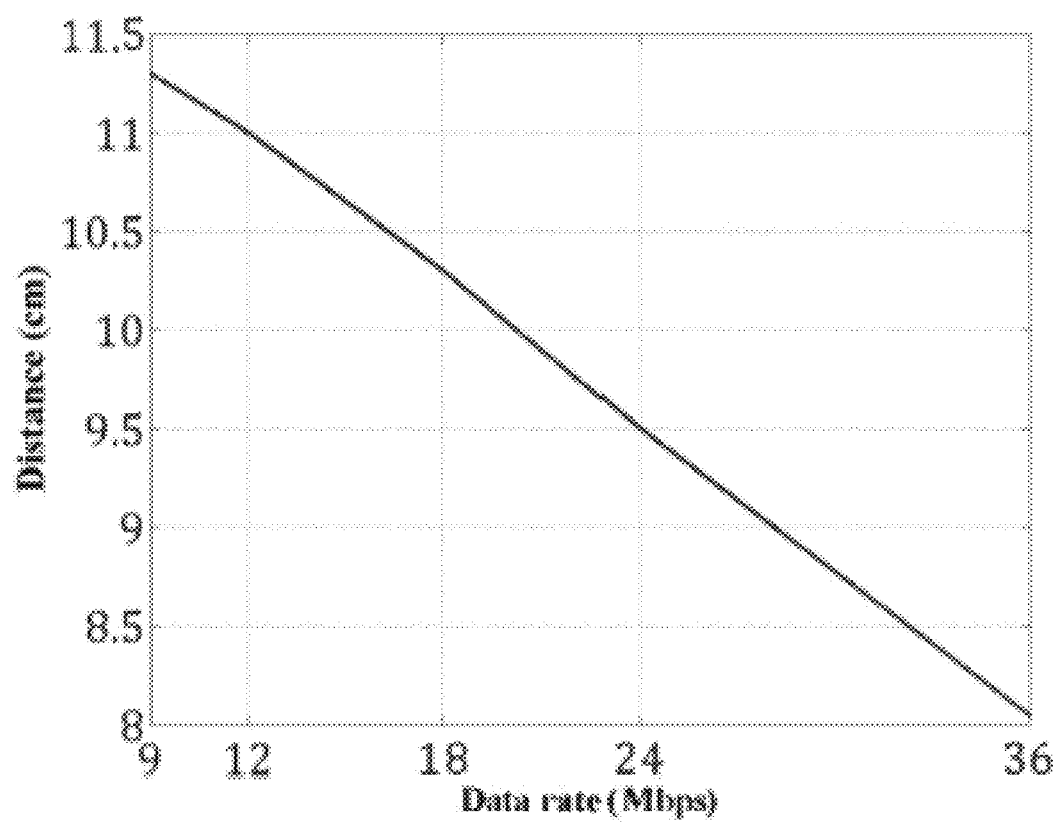
FIG. 7 is a graphical illustration showing achievable distance, as a function of bit rate, between in vivo and external antennas for a BER of $10^{-6}$.

The maximum achievable distance between transmit and receive antennas was also calculated as a function of the given data rates in the IEEE 802.11g. shown in FIG. 7. The calculation was performed using the maximum threshold power levels of 0.412 mW and a −101 dBm noise level at a BER of $10^{-6}$.

From the data found in this study, it is evident that there are limitations when transmitting at high frequencies from in vivo devices to ex vivo transceivers while still achieving reliable data transmission, since the maximum transmit power is restricted by SAR safety guidelines. When operating under low noise conditions with moderate BER requirements ($10^{-3}$), reliable data transmission to an external receiver can be achieved when located very close to the body. For cases when noise levels increase or the BER becomes more stringent, a relay network or the use of multiple receive antennas, such as in a SIMO system, may be necessarily to achieve high data rates.

The maximum SAR levels occur at points closest to the transmit antenna; thus, by placing the transmitter further from organs, the power levels could possibly be increased to obtain higher signal levels at the external receiver. In this example, the transmitter was located very close to the small intestine and the spine. Therefore higher BER should be achievable with proper placement of the in vivo transmitter (furthest possible distance from organs and tissues).

The test bench can be used by a person having ordinary skill in the art to further optimize the system design (e.g. using asymmetrical OFDM, MIMO transceivers, etc.) as well as the antenna architectures and location to meet BER requirements while always staying within the radiation safety guidelines.

Area Networks

Examples of networks that may be utilized to carry out certain embodiments of the current invention include, but are not limited to, a wireless local area network (WLAN), a wireless personal area network (WPAN), and a wireless body area network (WBAN). WLANs links two or more devices using a wireless distribution method, and usually provides a connection through an access point to the Internet. WPANs is a communication network for interconnecting devices centered around an individual person's workspace. Standards currently in use can be seen in Table 1:

TABLE 1

Standards of area networks currently in use.

| Standard | Max Data Rate (Mbps) | Range (m) | Bandwidth (MHz) | Comm. Technology |
|---|---|---|---|---|
| IEEE 802.11 A/B/G/N WiFi | 54-A/G 600-N | 50-100 | 20 40 | OFDM |
| Bluetooth v4.0 (Bluetooth Low Energy) | 0.200 | 10-50 | 2 | DSSS |
| IEEE 802.15.4 (Zigbee) | 0.250 | 10-100 | 5 | DSSS |
| IEEE 802.15.6 (WBAN) | 15.6 | <5 | 499.2 | Impulse Radio (IR), CP-BFSK |

Figure 8:
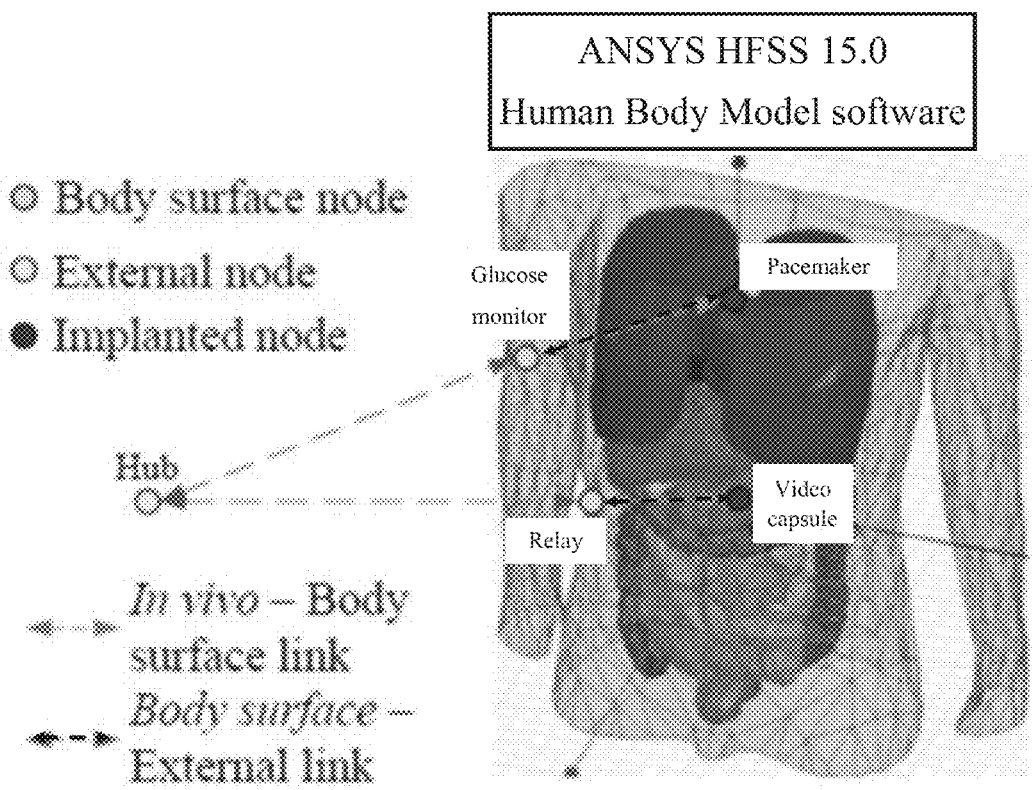
FIG. 8 is a human body model showing the hub (external node), body surface nodes (devices), and implanted nodes (devices), and the relationships therebetween.

A WBAN is a collection of low-power, intelligent devices, such as sensors or actuators, which are embedded, on-body, or in close proximity to the human body and are wirelessly interconnected. An exemplary illustration can be seen in FIG. 8, where an external link originates from the destination/hub and travels to the body surface nodes (glucose monitor and relay), where the node is a device. Subsequently, in vim body surface links originate from the glucose monitor and relay and travel to the implanted nodes (pacemaker and video capsule, respectively). Each WBAN can have one (1) hub and up to 64 nodes.

WBANs are receiving considerable attention because they can provide ubiquitous real-time monitoring, often without restricting the person's regular activities. A WBAN is a network formed by low power and limited-energy networked nodes that monitor vital human signs and are located in, on or around the human body. WBANs have certain operating characteristics and requirements, such as limited transmission and processing power (size, battery, and transmit power (SAR) limitations to avoid hazardous RF radiation to the human body, as well as to extend the node's battery lifetime), minimal or negligible latency, especially for real-time applications (in vivo video monitoring), and operation in in a highly lossy, dispersive, and time varying (due to the movement of internal fluids such blood) RF channel. An illustration of in vivo wireless communications and networking using WBAN can be seen in FIG. 9.

WBANs must satisfy stringent technical requirements, especially when the network is monitoring life-saving related signals such as indicators of a heart attack. A WBAN should be extremely reliable by avoiding single points of failure and providing self-healing capabilities if nodes or links are not operating properly, should have low power transmission to extend the network lifetime and preclude any harmful effects in the human body, and should maximize throughput over a lossy, dispersive, and dynamic channel. A frequent constraint is that it is often neither possible nor desirable to retransmit the sensor data.

A typical WBAN architecture can include a common MAC layer and three (3) physical layers. The common MAC layer generally has a MAC header, MAC frame body (0-255 octets) and FCS (2 octets). The MAC header can have seven (7) octets, including frame control (protocol version. ACK policy, security level, frame type, sequence number, etc.) being four (4) octets, recipient ID being one (1) octet, sender ID being one (1) octet, and BAN ID being one (1) octet. The three (3) physical layers can be PHY narrowband. PHY ultra wideband, and PHY human body communications (using skin as a conductor).

Regarding security, WBAN provides a self-contained, low-overhead, but strong security solution between nodes and hub. There is a master key generation through master key (MK) pre-shared association, unauthenticated association, public key hidden association, password-authenticated association, and display-authenticated association. There can be a simple two-way handshake for MK pre-shared association with elliptic curve cryptography (ECC) based for key agreement.

Figure 10:
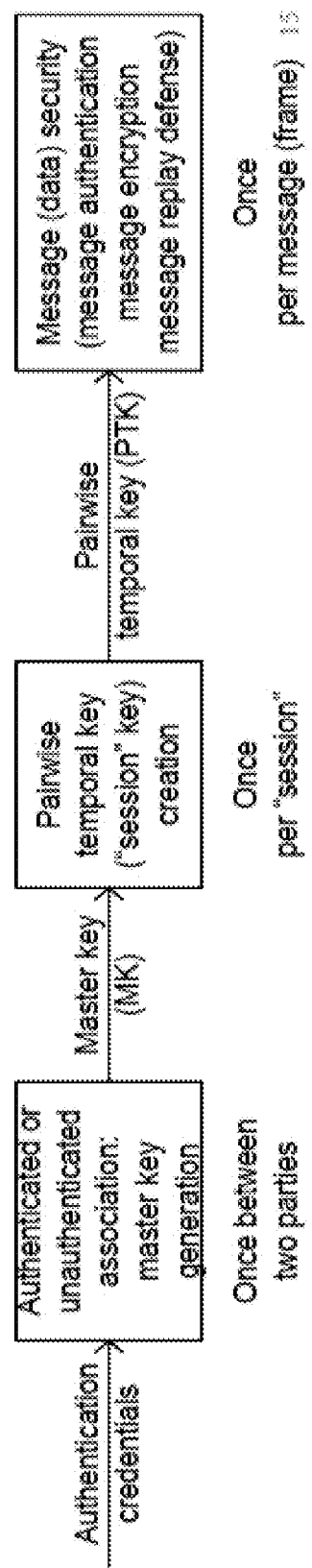
FIG. 10 is a flow diagram showing exemplary security measures used in WBANs.

A temporal key can also be created or distributed, including pairwise temporal key (PTK) creation for unicast protection and group temporal key (GTK) distribution for multicast/broadcast protection. Data authentication/encryption (e.g., AES-128 CCM) can also be used, allowing for replay prevention and low security overhead. FIG. 10 illustrates WBAN security.

The WBAN MAC layer may include prioritization of supported services, for example non-medical services, mixed medical and non-medical services, general health services, and highest priority medical services. An example priority mapping can be seen in Table 2.

TABLE 2

WBAN MAC layer priority map.

| Priority | User priority | Traffic designation | Frame type |
|---|---|---|---|
| Lowest | 0 | Background (BK) | Data |
| | 1 | Best effort (BE) | Data |
| | 2 | Excellent effort (EE) | Data |
| | 3 | Video (VI) | Data |
| | 4 | Voice (VO) | Data |
| | 5 | Medical data or network control | Data. or management |
| | 6 | High priority medical data or network control | Data or management |
| Highest | 7 | Emergency or medical event report | Data |

The PHY-dependent MAC sublayer, which uses standard wireless MACs, can include narrowband PHY (CSMA/CA). UWB PHY (CSMA/CA or Slotted Aloha, Hybrid ARQ (type II)), and HBC PHY (Slotted Aloha).

The PHY narrowband can include the following:
Channel coding [BCH (n=63, k=51)]→Add pad bits→Spreader→Bit interleaver→Scrambler→Symbol mapper

TABLE 3

PHY Narrowband.

| Frequency Band (MHz) | Modulation | Information Data Rate (kbps) | Support |
|---|---|---|---|
| 402-405 | π/2-DBPSK | 75.9 | Mandatory |
| (BW: 300 KHz) | π/2-DBPSK | 151.8 | Mandatory |
| Implantable | π/4-DBPSK | 303.6 | Mandatory |
| | π/8-DBPSK | 455.4 | Optional |
| 420-450 | GMSK | 75.9 | Mandatory |
| (BW. 320 KHz) | GMSK | 151.8 | Mandatory |
| | GMSK | 187.5 | Optional |
| 863-870 | π/2-DBPSK | 101.2 | Mandatory |
| 902-928 | π/2-DBPSK | 202.4 | Mandatory |
| 950-958 | π/4-DBPSK | 404.8 | Mandatory |
| (BW: 400 KHz) | π/8-DBPSK | 607.1 | Optional |
| 2360-2400 | π/2-DBPSK | 121.4 | Mandatory |
| 2400-2483.5 | π/2-DBPSK | 242.9 | Mandatory |
| (BW: 1 MHz) | π/2-DBPSK | 485.7 | Mandatory |
| | π/4-DBPSK | 971.4 | Mandatory |

The ultra-wideband (UWB) PHY specification is designed to offer robust performance for BANs and provide a large scope for implementation opportunities for high performance, robustness, low complexity, and ultra-low power operation. There are two PHY UWB technologies defined in the standard: Impulse radio (IR-UWB) and wideband FM (FM-UWB). IR-UWB is based on transmission of either a single pulse (new paradigm) or a burst of pulses (legacy) per information symbol. FM-UWB combines continuous phase binary FSK (CP-BFSK) modulation with wideband FM. The UWB PHY provides three levels of functionality: (1) Activation and deactivation of the radio transceivers. (2) The UWB PHY may provide clear channel assessment (CCA) indication to the MAC in order to verify activity in the wireless medium. (3) The PLCP constructs the PHY layer protocol data unit (PPDU) by concatenating the synchronization header (SHR), physical layer header (PHR) and physical layer service data unit (PSDU). The transmit order proceeds in the order of SHR, PHR, and PSDU.

TABLE 4

Ultra Wideband (UWB).

| Band group | Channel number | Center frequency (MHz) | Bandwidth (MHz) | Channel attribute |
|---|---|---|---|---|
| Low band | 1 | 3494.4 | 499.2 | Optional |
| | 2 | 3993.6 | 499.2 | Mandatory |
| | 3 | 4492.8 | 499.2 | Optional |
| | 4 | 6489.6 | 499.2 | Optional |
| | 5 | 6988.8 | 499.2 | Optional |
| | 6 | 7488.0 | 499.2 | Optional |
| High band | 7 | 7987.2 | 499.2 | Mandatory |
| | 8 | 8486.4 | 499.2 | Optional |
| | 9 | 8985.6 | 499.2 | Optional |
| | 10 | 9484.8 | 499.2 | Optional |
| | 11 | 9984.0 | 499.2 | Optional |

The PHY narrowband can include the following:
Scrambler→Channel coding [BCH (n=63, k=51)]→Pad bits→Spreader→Bit interleaver

TABLE 5

Impulse Radio (IR), On-Off signaling

| Uncoded bit rate (Mbps) | FEC rate | Coded bit rate (kbps) |
|---|---|---|
| 0.487 | 0.81 | 394.8 |
| 0.975 | 0.81 | 789.7 |
| 1.950 | 0.81 | 1,579.0 |
| 3.900 | 0.81 | 3,159.0 |
| 7.800 | 0.81 | 6,318.0 |
| 15.600 | 0.81 | 12,636.0 |

TABLE 6

Impulse Radio (IR), DBPSK/DQPSK modulations

| Mod | Uncoded bit rate (Mbps) | FEC rate | Coded bit rate (kbps) |
|---|---|---|---|
| DBPSK | 0.487 | 0.5 | 243.0 |
| DBPSK | 0.975 | 0.5 | 457.0 |
| DBPSK | 1.950 | 0.5 | 975.0 |
| DBPSK | 3.900 | 0.5 | 1,950.0 |
| DBPSK | 7.800 | 0.5 | 3,900.0 |
| DBPSK | 15.600 | 0.5 | 7,800.0 |
| DBPSK | 0.557 | 0.5 | 278.0 |
| DQPSK | 1.114 | 0.5 | 557.0 |

TABLE 7

| FM (optional), FM-UWB data rate | | |
|---|---|---|
| Uncoded bit rate (Mbps) | FEC rate | Coded bit rate (kbps) |
| 250 | 0.81 | 202.5 |

Figure 11:
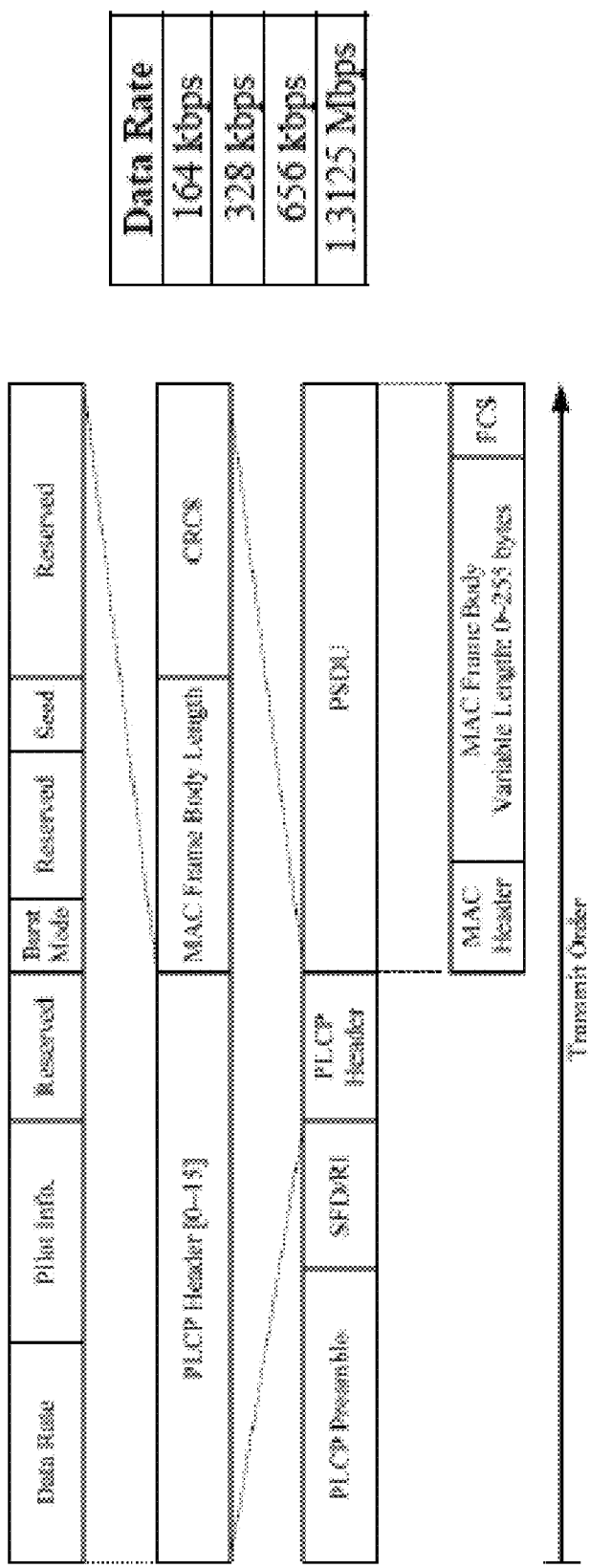
FIG. 11 is a diagram showing PHY human body communications.

The PHY human body communications specification is for human body communications (HBC) physical layer (PHY) that uses the electric field communication (EFC) technology. The electrode in contact with the body is used for transmitting or receiving an electrical signal through the body to a device (e.g., smartphone). The band of operation can be centered at about 21 MHz. FIG. 11 illustrates the PHY human body communications.

In an embodiment, within the medical implant communication service, a frequency of about 402 MHz to about 405 MHz can be allocated (per the FCC), as this range can provide reasonable signal propagation characteristics in the human body.

TABLE 8

| Frequency data for medical implant communication service. | | | |
|---|---|---|---|
| Frequency Band (MHz) | Number of Channels | Channel Bandwidth | Typical Data Rates |
| 402-405 | 10 | 300 KHz | 75.9-455.4 Kbps |

In this case, a short-range, wireless link may be desired to connect low-power implanted medical devices with monitoring and control equipment. Implanted medical devices include, but are not limited to, cardiac pacemakers, implantable cardioverter/defibrillator (ICD), neuro-stimulators, etc.

As the foregoing data illustrates in terms of the current invention, certain embodiments address the need for higher data rate communications. Currently, with conventional technologies, traditional implants use inductive links, have a limited range (in contact with patient), have low frequency (data rates similar to a dial-up computer modem), and low data rate communications in the MICS band (75.9-455.4 Kbps). Using certain embodiments of the current invention, however, provide higher data rates, upload patient events captured in the IMD's memory to the base station for analysis, and shorten doctor-patient consultancy times.

In Vivo Wireless Channel Characterization and Signal Processing

Software can be utilized to simulate the RF channel. Such simulations are key to providing general results and intuition before experimentally sounding channels. The experimental channel sounding, with phantoms and live models, can then provide raw data samples of the in vivo channel itself and lead to useful datasets. More useful are parametric models that can iteratively evolve based on the simulations and experimental measurements. Such models improve the ability to pursue endeavors in the biomedical device field specifically with regards to wireless communications from in vivo devices. Given data from simulated, measured, and modeled channels, a thorough analysis includes benefit/cost behavior of implanted devices, performance as a location of devices in the body, power consumption, and degree of invasiveness. Once point-to-point communications are well understood, the possibilities of networking in vivo nodes can be examined. The modality/scenario combinations can then be tested in phantoms and live models (porcine subjects) to determine effectiveness.

Well-studied wireless environments include, for example, cellular, WLAN, and deep-space. Because of near-field effects (at low operating frequencies) and multipath scattering (at high operating frequencies) with propagation through different types of human organs and internal structures between closely spaced transmitter and receiver antennas, characterizing in vivo wireless propagation facilitates optimization of communications and requires familiarity with both the engineering and the biological environments.

Free Space and In Vivo Attenuation

Simulated attenuation in HFSS was achieved, where a signal travels from a monopole placed inside the abdomen to an external monopole with a 30 cm transmission path (9 cm of the path are inside the body). Antenna effects have been removed in software by simultaneously matching each antenna port impedance in Agilent ADS. Signal loss can be seen in FIG. 12 for in vivo attenuation and free space loss. As can be seen, attenuation drop-off rate is not constant and is seen to increase more rapidly above 2.2 GHz.

In Vivo Attenuation and Dispersion

Figure 12:
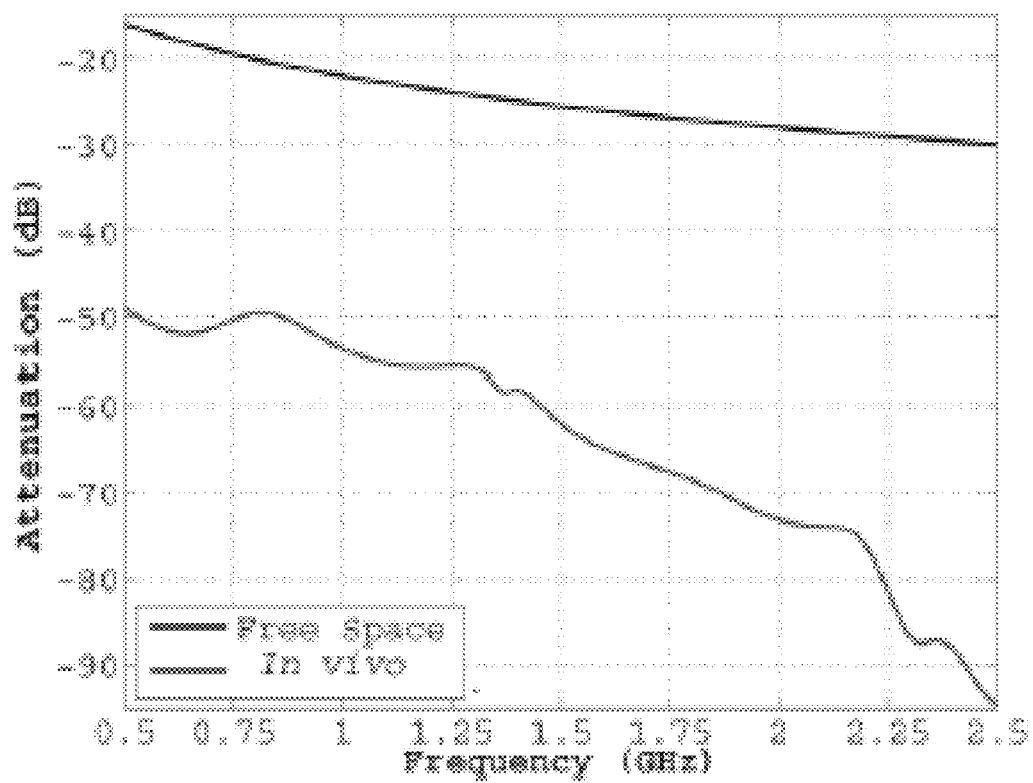
FIG. 12 is graphical illustration of signal loss for in vivo attenuation versus free space loss.
Figure 13B:
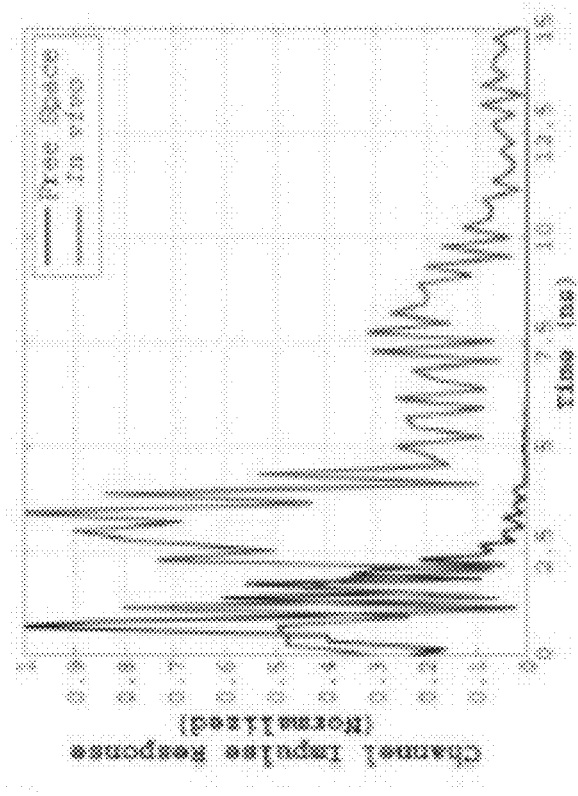
FIG. 13B is a graphical illustration showing normalized channel impulse response over time for the human body for free space and scattered environments.
Figure 13A:
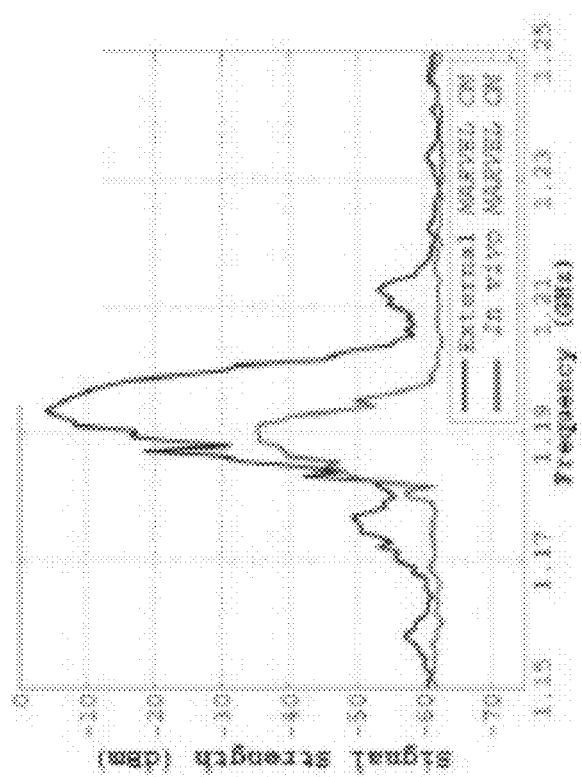
FIG. 13A is a graphical illustration of results of a vivarium experiment using a MARVEL CM showing differences in signal strength between the in vivo and external measurements.

To test in vivo attenuation and dispersion, the carrier frequency was about 1.2 GHz and the video signal bandwidth was 5 MHz. The FM modulation bandwidth was about 11 MHz. The transmitter was located inside the abdominal cavity. The receiver was placed about 0.5 m from the transmitter in front of the abdomen. In FIGS. 13A-13B, it can be seen that there is about a 30 dB difference in signal strength between the in vivo and the external measurement, which shows that there is approximately 30 dB of attenuation through the organic tissue. This seems to be in good agreement in what is shown in FIG. 12. In vivo time dispersion is much greater than expected from the physical dimensions.

In Vivo Wireless Channel Directional Properties

Figure 14A:
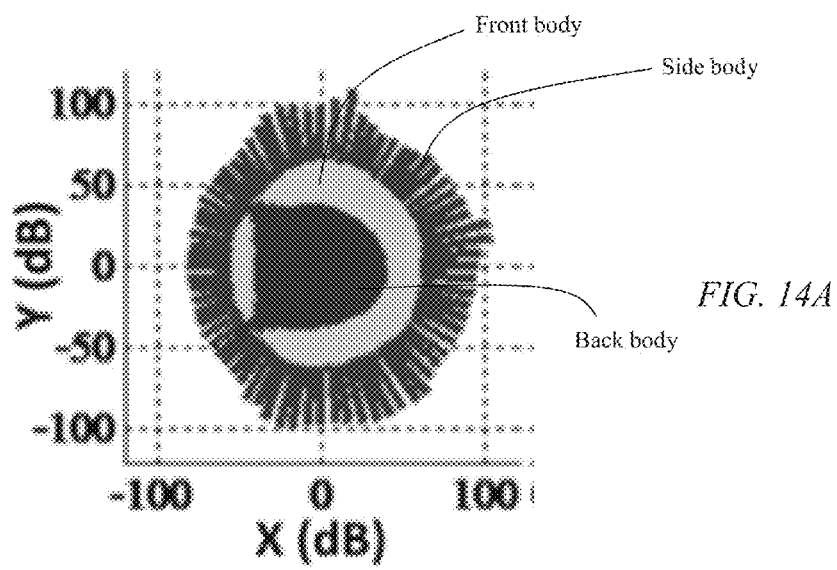
FIG. 14A is a graphical illustration of path loss as a function of position for the human body with the transmitter at (0,0) and measured at a height of 1.1 m. The attenuation at any point (x,y) is $[(P_x)^2+(P_y)^2]^{1/2}$.
Figure 14B:
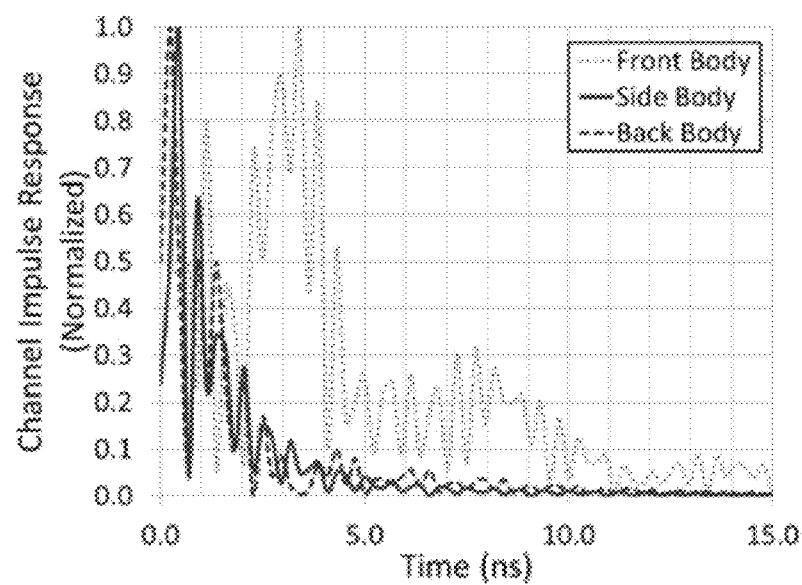
FIG. 14B is a graphical illustration of channel impulse response for the human body for different locations of the receiver.

One of the many differences between classic RF models and the in vivo channel is that the path loss and impulse response is a function of the direction (receiver location). As seen in FIGS. 14A-14B, the path loss is a function of the frequency and not homogenous around the body. Moreover, the angular dependency is noticeable for 500 MHz. The distance between transmitter and receiver is 30 cm with center frequencies of 2 GHz (side body), 1 GHz (front body), and 0.5 GHz (back body).

MIMO In Vivo

Figure 15A:
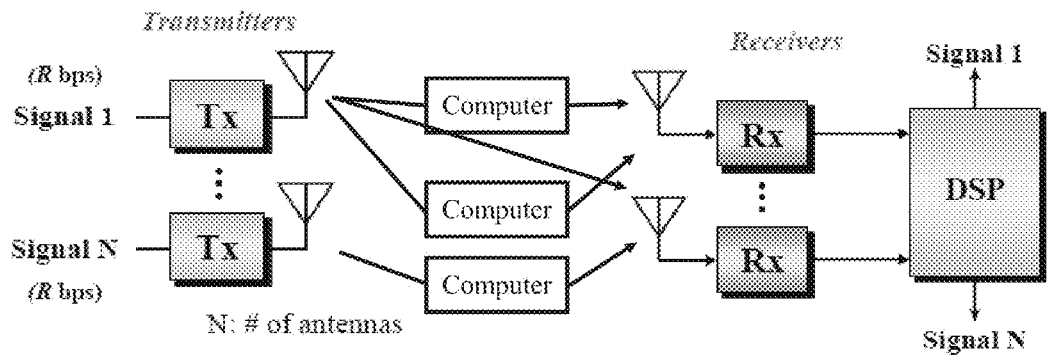
FIG. 15A is schematic showing multiple transmit and receive antennas (MIMO).
Figure 15B:
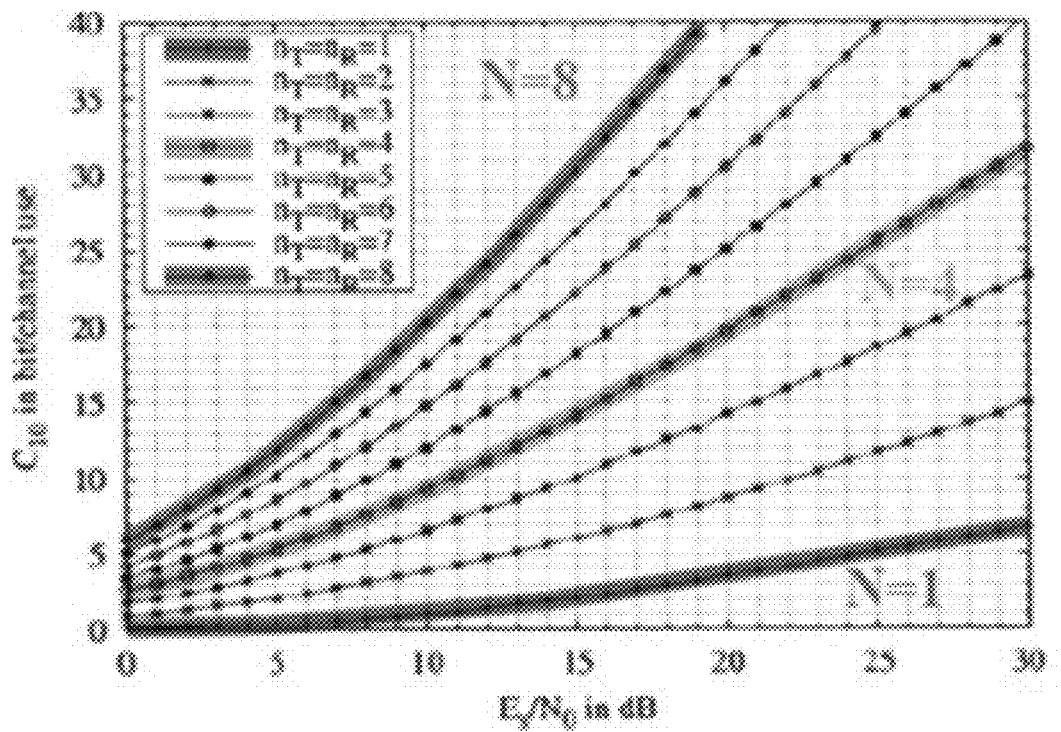
FIG. 15B is a graphical illustration showing capacity increase with an increase in number of channels without increasing total power.

A multiple-input and multiple-output system is contemplated for in vivo communications. In particular, multiple transmit and receive "smart" antennas can increase wireless capacity. As seen in FIG. 15A, a multipath scattering scrambles the signals, each receiver having a different combination of signals. A digital signal processing algorithm de-scrambles the received signal to reproduce the original signals and deliver the energy to the target receiver. As seen in FIG. 15B, capacity increases about linearly with the number of antennas with no increase in total power.

Figure 16:
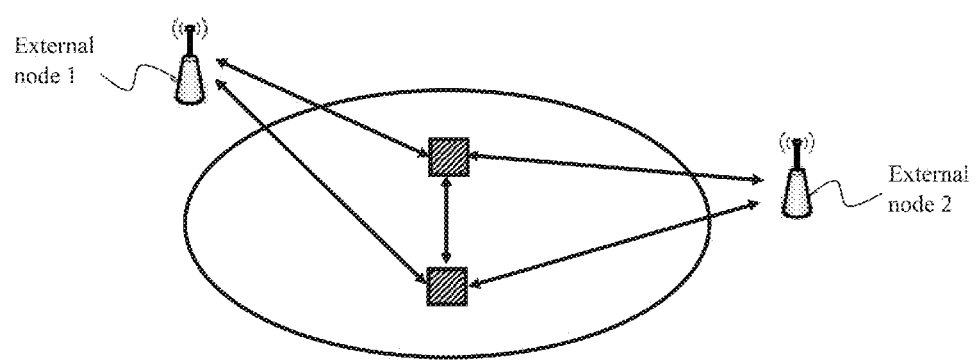
FIG. 16 is a schematic showing cooperative MIMO in vivo.

MIMO techniques, such as the schematic seen in FIG. 16, may be used to interrogate power-limited, or passive, sensors. If feasible, this could have the potential dual benefit of not only enhancing the data rates possible through spatial multiplexing. Advantages can include, for example, increased read reliability using spatial diversity, increased read range and throughput, no increase in power consumption with higher data rate, and full channel information at the reader through sensor backscatter. A contemplated application of this technique is RFID for passive devices.

Network Coding

Figure 17:
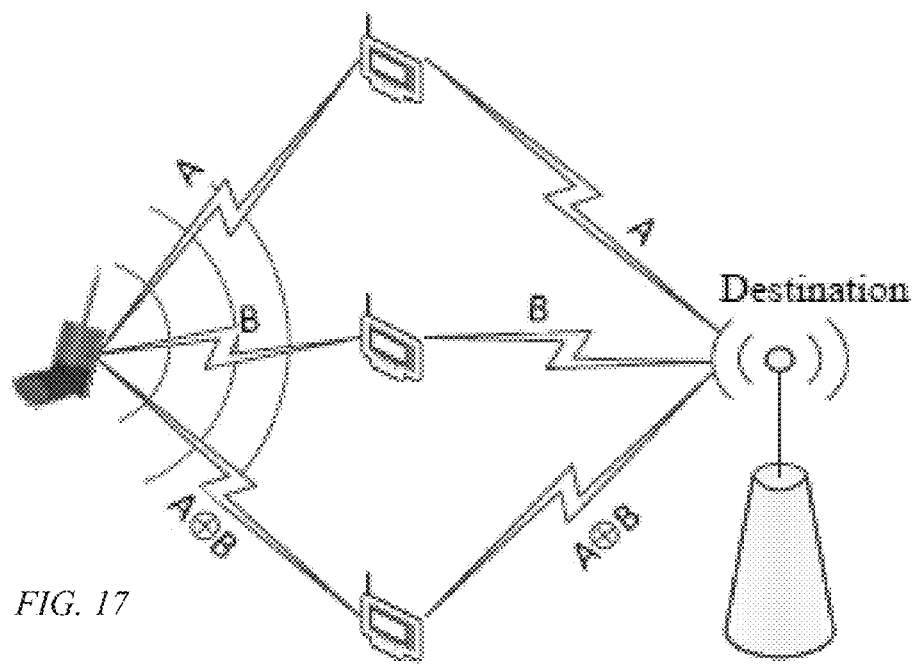
FIG. 17 is a schematic showing network coding.

Network coding (NC), as indicated in FIG. 17, achieves capacity gain through coding of information, making reliable networks/systems out of relatively unreliable subsystems.

NC improves network reliability against packet losses and link failures (and coding provides some security against casual or malicious listeners/intruders) by transmitting different forms data down multiple paths, such that even if one or more paths fail to deliver their information, the data still reaches the recipient which can deduce the data.

Wireless Miniature Anchored Robotic Videoscope for Expedited Laparoscopy (MARVEL) Camera Module (CM)

Figure 18:
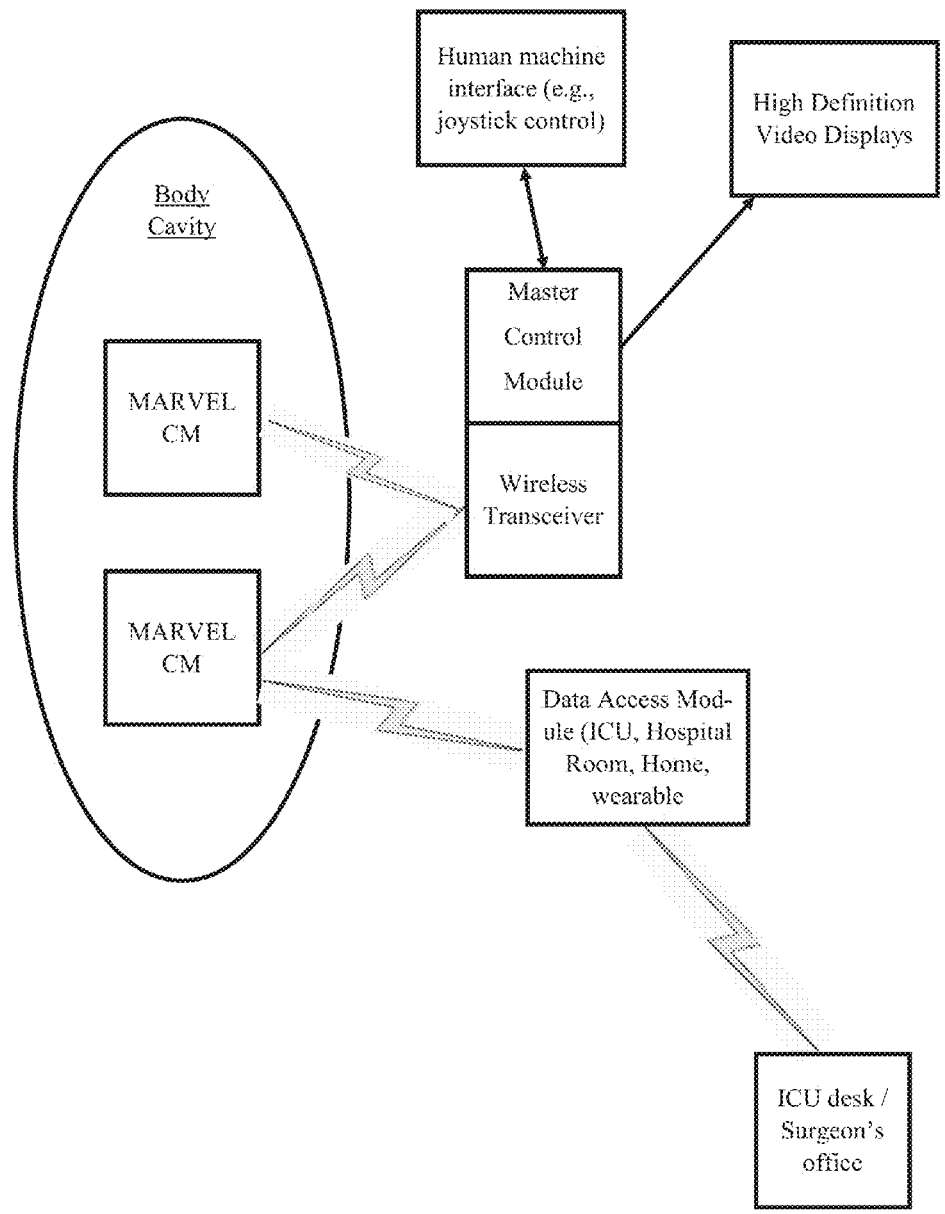
FIG. 18 is a schematic showing a configuration of the MARVEL system.

The MARVEL system is a wirelessly controlled and communicating high-definition video system that provides the spatial and visual advantages of open-cavity surgeries. As seen in FIG. 18, the MARVEL system included (1) multiple CMs with wirelessly controlled pan/tilt enabling a full hemisphere field of view inside the abdominal cavity, wirelessly adjustable focus, and a multi-wavelength illumination control system; a Master Control Module (MCM) that provides a near-zero latency video wireless communications, independent wireless control for multiple MARVEL CMs, digital zoom; and a wireless human-machine interface (HMI) that controls the CM functions. U.S. Pat. No. 8,416,342 further describes imaging devices of this nature and is incorporated herein by reference.

The MARVEL CM is an example of one device that can be used in a family of wirelessly networked in vivo biosensors and actuators that are capable of wirelessly communicating to one or more external nodes. By accomplishing this, the system has particular advantages and benefits including, but not limited to, decreasing the surgical-tool bottleneck experienced by surgeons in laparo-endoscopic single-site surgical procedures; eliminating power, video, and light source cabling issues in current laparoscopes; increasing the dexterity and fine motion options for the surgeon; and increasing the imaging angle and the usable workspace inside the abdominal cavity.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A system for performing networked medical procedures on a subject, comprising:
   a plurality of in vivo medical devices, said plurality of in vivo medical devices including an in vive transmitter that is positioned to maximize bit-error-rate;
   a network providing a communication path between a first in vivo medical device and a second in vivo medical device each selected from the plurality of in vivo medical devices, said network comprising a relay network or a plurality of receive antennas, said network permitting said first in vivo medical device to receive a first control signal and to transmit a second control signal from said first in vivo medical device to said second in vivo medical device over said communication path; and
   an ex vivo control unit to control the behavior of the plurality of in vivo medical devices, said behavior including spatial parameters of said plurality of in vivo medical devices;
   said network providing a wireless communication path between the control unit and at least one of the plurality of in vivo medical devices.

2. The system of claim 1, further comprising:
   a second wireless communication path between at least one of the plurality of in vivo medical devices and an ex vivo system.

3. The system of claim 1, wherein the control unit is a magnet.

4. The system of claim 1, wherein the control unit is an electronic device that generates control signals.

5. The system of claim 1, wherein the control unit is an electronic device that generates communication signals.

6. The system of claim 1, wherein each of the plurality of in vivo medical devices are one or more medical devices chosen from the group consisting of an imaging device, a sensor, a power source, and a cutting tool.

7. The system of claim 1, wherein the communication path between the at least two in vive medical devices is wireless.

8. The system of claim 1, wherein the communication path between the at least two in vivo devices is wired.

9. The system of claim 1, wherein each of the plurality of in vive medical devices is separately wirelessly addressable and controllable.

10. The system of claim 1, further comprising:
    a plurality of wireless communication paths between the control unit and each of the plurality of in vivo medical devices.

11. The system of claim 1, further comprising:
    said communication path including a signal having a specific absorption rate less than or equal to 0.08 W/kg.

12. The system of claim 1, further comprising:
    said positioning of said in vivo transmitter being furthest from organs and tissues within said subject.

13. The system of claim 1, further comprising:
    said network being a Layer 3 data network.

14. The system of claim 1, further comprising:
    said behavior of said plurality of in vivo medical devices including spatial parameters of said plurality of in vivo medical devices.

15. The system of claim 1, further comprising:
    said ex vivo control unit being an expert system.

16. A method of performing networked medical procedures comprising:
    providing a plurality of in vivo medical devices, said plurality of in vivo medical devices including an in vivo transmitter that is positioned to maximize bit-error-rate;
    establishing a network that provides a communication path between a first in vivo medical device and a second in vivo medical device each selected from the plurality of in vivo medical devices, said network comprising a relay network or a plurality of receive antennas, said network permitting said first in vivo medical device to receive a first control signal and to transmit a second control signal from said first in vivo medical device to said second in vivo medical device over said communication path;
    providing an ex vivo control unit to control the behavior of the plurality of in vivo medical devices, said behavior including spatial parameters of said plurality of in vivo medical devices;

said network providing a wireless communication path between the control unit and at least one of the plurality of in vivo medical devices; and controlling the behavior of the plurality of in vivo medical devices from outside the body using the wireless communication path between the control unit and the at least one of the plurality of in vivo medical devices.

17. The method of claim 16, further comprising:

providing a second wireless communication path between at least one of the plurality of in vivo medical devices and an ex vivo system.

18. The method of claim 17, wherein the second wireless duplex communication path is a duplex communication path.

19. The method of claim 16, wherein controlling the behavior of the plurality of in vivo medical devices from outside the body using the wireless communication path between the control unit and the at least one of the plurality of in vivo medical devices, comprises:

generating a control signal at the control unit; and transmitting the control signal over the wireless communication path to a first in vivo medical device of the plurality of in vivo medical devices.

20. The method of claim 19, wherein controlling the behavior of the plurality of in vivo medical devices from outside the body using the wireless communication path between the control unit and the at least one of the plurality of in vivo medical devices, further comprises:

receiving the control signal at the first in vivo medical device;

generating a second control signal at the in vive medical device; and transmitting the second control signal over the communication path between the first in vivo medical device and a second in vivo medical device to the second in vivo medical device.

* * * * *

UNITED STATES PATENT AND TRADEMARK OFFICE
CERTIFICATE OF CORRECTION

Page 1 of 1

PATENT NO. : 8,923,773 B1
APPLICATION NO. : 14/099428
DATED : December 30, 2014
INVENTOR(S) : Richard D. Gitlin et al.

It is certified that error appears in the above-identified patent and that said Letters Patent is hereby corrected as shown below:

In the Claims,

Column 17, Claim 1, Line 59 should read:

vivo medical devices including an in vivo transmitter

Column 18, Claim 7, Line 26 should read:

between the at least two in vivo medical devices is wireless.

Column 18, Claim 9, Line 30 should read:

vivo medical devices is separately wirelessly addressable and

Column 20, Claim 20, Line 12 should read:

generating a second control signal at the in vivo medical

Signed and Sealed this
Twenty-first Day of April, 2015

Michelle K. Lee
*Director of the United States Patent and Trademark Office*